United States Patent [19]

Grunwell et al.

[11] 4,000,273
[45] Dec. 28, 1976

[54] METHOD FOR THE CONTROL OF FERTILITY
[75] Inventors: Joyce F. Grunwell, Hamilton; Harvey D. Benson, Cincinnati, both of Ohio
[73] Assignee: Richardson-Merrell Inc., Wilton, Conn.
[22] Filed: Oct. 9, 1975
[21] Appl. No.: 621,207

Related U.S. Application Data

[62] Division of Ser. No. 411,791, Nov. 1, 1973, Pat. No. 3,928,398.
[52] U.S. Cl. .......................... 424/238; 260/397.5; 424/241
[51] Int. Cl.² ...................................... A61K 31/56
[58] Field of Search ................. 424/238; 260/397.5

[56] References Cited
UNITED STATES PATENTS 3,846,456   11/1974   Campbell et al. .............. 260/397.3

Primary Examiner—Elbert L. Roberts
Attorney, Agent, or Firm—William J. Stein; Eugene O. Retter; George W. Rauchfuss, Jr.

[57] ABSTRACT

7α-Methylestr-4-ene-3α,17β-diol and derivatives thereof useful as antifertility agents.

4 Claims, No Drawings

METHOD FOR THE CONTROL OF FERTILITY

This is a division, of application Ser. No. 411,791, filed Nov. 1, 1973, now U.S. Pat. No. 3,928,398.

FIELD OF THE INVENTION

This invention relates to 7α-methylestr-4-ene-3α,17β-diol and novel derivatives thereof, to their preparation and to their usefulness as antiprogestational and antifertility agents.

BACKGROUND OF THE INVENTION

Among the steroid hormones progesterone is unique inasmuch as its presence is important in female mammals, particularly in women, for the maintenance of a successful pregnancy. A loss or interference with progesterone during the early stages of mammalian pregnancy prevents the continuation of gestation. Indeed, the loss of progesterone in the very early stages of a human pregnancy prevents either the implantation of the blastocyst or results in the subsequent expulsion of a newly implanted blastocyst.

Applicants have made the important discovery that the compounds of the present invention exhibit marked antiprogestational and antifertility properties without substantial interference with other biological processes. Thus, under certain dosage regimens, as for example, a daily, low-dosage regimen, the instant compounds are able to reduce fertility in mammals as a consequence of their antiprogestational activity without interfering with normal ovulation. In this regard these compounds differ from the contraceptive steroids of the prior art which function by inhibiting ovulation, by interfering with ovum transport or by virtue of their progestational and/or estrogenic properties.

Administration of the antiprogestational agents of the present invention during the normal menstrual cycle of primates apparently causes a desynchronization of the maturing uterine mucosa relative to the process of ovulation, thereby preventing implantation or nidation of the fertilized ovum. Thus, in women, for example, the withdrawal of progesterone from a progesterone-primed endometrium results in menstrual bleeding. Periodic administration of the antiprogestational agents of the present invention, therefore, insures menstrual cyclicity in women, even when administered subsequent to ovulation.

DESCRIPTION OF PRIOR ART

U.S. Pat. No. 3,301,879 represents the closest art known to applicants and discloses a series of 7α-lower alkyl-4-estrene-3β,17β-diols as anabolic, androgenic agents, antigonadotropic agents, gestagenic agents and anti-hypercholesterinemic agents and specifically discloses the compound Δ⁴-3:17-dihydroxy-7α-methyl-19-norandrostene.

All of the compounds described in U.S. Pat. No. 3,301,879 contain either a substituent in the 3-position whose stereochemistry is not designated, or contain a substituent in the 3-position which is specifically designated as being in the β-configuration. None of the species described therein have a 3-substituent designated to be in the α-configuration. These compounds are prepared by reducing the 4-estren-3-one with a complex light metal hydride, as for example, lithium, sodium, potassium or calcium borohydride, or the 4-estren-3-one can be reduced with lithium aluminum hydride or an alkali triloweralkoxyboron or aluminum hydride, such as sodium trimethoxyborohydride or lithium tri-tertiarybutoxyaluminum hydride. Such reagents are known to predominately produce the 3β-equatorial isomer, cf., Reduction of 3-keto-Δ⁴-steroids with lithium aluminum hydride, sodium borohydride, and lithium tri-t-butoxyaluminum hydride, Fried and Edwards, Organic Reactions in Steroid Chemistry, Volume 1, pp. 75–81, Van Nostrand, Reinhold Company, 1972.

U.S. Pat. No. 3,413,287 discloses a series of (optionally 17-alkylated) 7α-methyl-4-estrene-3β,17β-diols as anabolic, androgenic, estrogenic and antiestrogenic agents. These compounds are essentially prepared in the same manner as the compounds described in U.S. Pat. No. 3,301,879 above, i.e., the reduction of 7α-methylestr-4-en-3-ones using a metallic reducing agent such as lithium aluminum hydride, sodium borohydride, lithium tri(tertiarybutoxy)aluminum hydride or diisobutylaluminum hydride to form the 3β-hydroxy-4-ene derivatives. No compounds were disclosed having a 3-substituent in the α-configuration. Example 1, for example, specifically describes the preparation of 7α-methylestr-4-ene-3α,17β-diol, melting at 99°–101° C.

The use of sodium trialkylborohydride as a reducing agent is known. Brown and Krishnamurthy, J. Amer. Chem. Soc., 94, 7159 (1972) and Brown, ibid, 95, 4100 (1973), teach the use of a hindered lithium tri-sec-butylborohydride as a stereoselective reducing agent for certain monocyclic and bicyclic ketones. The monocyclic ketones described therein are relatively simple alkyl-substituted cyclopentanones and cyclohexanones. Only two bicyclic ketones were reduced, namely, camphor and norcamphor, which are unrelated to the 3-oxo steroids being reduced in accordance with the present invention.

SUMMARY OF THE INVENTION

This invention relates to a novel class of steroids. More particularly, this invention relates to essentially pure 7α-methylestr-4-ene-3α,17β-diols which are useful as antiprogestational and antifertility agents and which can be represented by the general formula

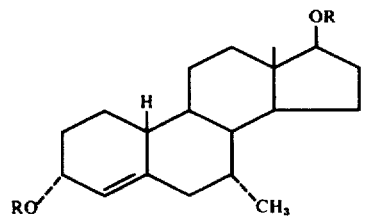

wherein each R is selected from the group consisting of hydrogen, acyl having from 1 to 12 carbon atoms, trialkylsilyl in which the alkyl group contains from 1 to 4 carbon atoms, 1-cycloalkenyl having from 5 to 8 carbon atoms, 1-methoxycycloalkyl and 1-ethoxycycloalkyl in which the cycloalkyl group has from 5 to 8 carbon atoms and 2-tetrahydropyranyl.

In general the compounds of the present invention are prepared by the reduction of the corresponding 17β-hydroxy-7α-methylestr-4-en-3-one using a highly hindered lithium trialkylborohydride.

A variety of compositions and methods for the control of fertility utilizing these novel compounds are also included within the scope of the present invention.

DETAILED DESCRIPTION OF THE INVENTION

As illustrated by general Formula (I) above, the novel compounds of the present invention all share a 7-methyl substituent which is in the α-configuration of the class of estrane steroids. Additionally, these compounds all have an unsaturation present in the 4-position and share hydroxyl groups or substituted hydroxyl groups in the 3α and 17β-configurations. Consequently, all of the instant compounds can be considered either as 7α-methylestr-4-ene-3α,17β-diols or derivatives thereof, more particularly certain mono- and di-ester and ether derivatives thereof.

As seen from the description of general Formula (I) above, both hydroxyl groups can be unsubstituted, as in the case of the parent compound 7α-methylestr-4-ene-3α,17β-diol. Alternatively, one of the hydroxyl groups can be substituted as for example, 3α-acetoxy-17β-hydroxy-7α-methylestr-4-ene or 3α-hydroxy-17β-acetoxy-7α-methylestr-4-ene; or both of the hydroxyl groups may be substituted, as for example, the compound 3α,17β-diacetoxy-7α-methylestr-4-ene.

The acyl esters which are present are obtained from hydrocarbon acyl radicals having from 1 to 12 carbon atoms inclusively. The organic acyl groups include those of saturated and unsaturated aliphatic acids and aromatic acids such as formic, acetic, propionic, butyric, isobutyric, valeric, isovaleric, caproic, caprylic, decanoic, dodecanoic, acrylic, crotonic, cyclobutanecarboxylic, cyclopentanecarboxylic, cyclopentenecarboxylic, cyclohexanecarboxylic, benzoic, toluic, naphthoic, ethylbenzoic, phenylacetic, naphthaleneacetic, phenylvaleric, cinnamic, phenylpropionic, p-propyloxyphenylpropionic and p-butyloxyphenylacetic acid.

The ether derivatives which are present include unsaturated cycloalkane ethers having from 5 to 8 carbon atoms in which the unsaturation is present in a position α to the ether oxygen. Illustrative of such unsaturated ethers are the 1-cyclopentene, 1-cyclohexene, or 1-cyclooctene radicals. In addition, the corresponding saturated cycloalkanes are also included within the scope of this invention wherein the cycloalkane group is substituted with a methoxy or ethoxy radical at its point of attachment. Illustrative of such saturated substituted cycloalkane ethers are: 7α-methyl-17β-(1'-methoxycyclopentyloxy)-4-estren-3α-ol, 7α-methyl-3α,17β-di(1'-ethoxycyclohexyloxy)-4-estrene, and 7α-methyl-3α-(1'-methoxycyclohexyloxy)-4-estren-17β-ol acetate. Included within the class of ether derivatives are the saturated heterocyclic 2-tetrahydropyranyl ethers, as for example, 7α-methyl-17β-(2'-tetrahydropyranyloxy)-4-estren-3α-ol. Lastly, the trialkylsilyl ethers such as the trimethylsilyl and dimethyl t-butylsilyl ethers are also included within the purview of the present invention, as for example the compounds 7α-methyl-17β-trimethylsiloxy-4-estren-3α-ol and 7α-methyl-3α,17β-di(trimethylsiloxy)-4-estrene.

The following compounds further illustrate the species represented by general Formula I above: 7α-methylestr-4-ene-3α,17β-diol 3-acetate, 7α-methyl-17β(2'-tetrahydropyranyloxy)estr-4-en-3α-ol, 3α-(1'-cyclopentenyloxy)-7α-methylestr-4-en-17β-ol, 7α-methylestr-4-ene-3α,17β-diol 17-heptanoate, 17β-(1'-methoxycyclohexyloxy)-7α-methylestr-4-en-3α-ol, 3α-(1'-cyclohexenyloxy)-7α-methylestr-4-en-3α-ol 3-butyrate, 7α-methylestr-4-ene-3α,17β-diol 3,17-dipropionate, 7α-methyl-3α,17β-di(2'-tetrahydropyranylox y)estr-4-ene, 3α-(1'-ethoxycycloheptyloxy)-7α-methylestr-4-en-17β-ol 17-acetate, 7α-methyl-3α-trimethylsilyloxyestr-4-en-17β-ol, 7α-methylestr-4-ene-3α,17β-diol 3-dodecanoate, and 7α-methyl-3α,17β-di(trimethylsilyloxy)estra-4-ene.

The preferred compound of the present invention is 7α-methylestr-4-ene-3α,17β-diol. Applicants have discovered a novel process for the reduction of 17β-hydroxy-7α-methylestr-4-en-3-one using a highly hindered lithium trialkylborohydride which produces the 3α-hydroxy isomer. This compound is closely related to the corresponding 3β-hydroxy isomer known to the prior art in the references previously cited. In accordance with the teachings of Example 2 of U.S. Pat. No. 3,301,879, a "crude crystalline Δ⁴-3:17-dihydroxy-7α-methyl-19-norandrostene" would be obtained. This equivocally identified compound is in reality the compound Δ⁴-3β,17β-dihydroxy-7α-methyl-19-norandrostene, or using applicants' preferred system of nomenclature, the compound, 7α-methylestr-4-ene-3β,17β-diol. A comparison with Example 1 of the same patent in which a similar reduction is conducted on the 7α,17α-dimethyl analogue would lead a person having ordinary skill in the art to believe that the 3α-isomer is obtained inasmuch as Example 1 specifically indicates the configuration of the product to be in the 3β-position. Additionally, Example 1 of U.S. Pat. No. 3,413,287 specifically teaches the preparation of 7α-methylestr-4-ene-3β,17β-diol, having a melting point of 99°–101° C, using essentially the same starting material and reduction procedure. Although traces of the 3α-hydroxy isomer may be present in the reaction mixtures of the prior art, the art is devoid of any suggestion of the preparation and isolation or of the advantages obtained with the essentially pure 3α-hydroxy isomer.

The 7α-methylestr-4-en-3α,17β-diol is readily prepared by the reduction of the corresponding 4-estren-3-one using a highly hindered lithium trialkylborohydride. By the term highly hindered is meant a large or bulky organic radical which imparts an enzyme-like stereoselectivity to the reducing agent. The highly hindered nature of this class of reducing agents is essential in order to achieve a stereoselective reduction to the 3α-hydroxy isomer. Generally speaking, the more hindered the reagent becomes, the greater its degree of stereoselectivity with, however, a concommitant loss in reaction rates. The reduction is not considered to be a true stereospecific reduction inasmuch as some of the 3β-hydroxy isomer is also obtained. Nevertheless, these highly hindered trialkylborohydrides are selective nucleophilic reducing agents which will reduce the 3-ketones with simple efficiency and with a high degree of stereoselectivity to provide a ready means for the preparation of the difficulty obtainable 3α-hydroxy isomers. Illustrative of the highly hindered reducing agents which may be employed are the lithium or potassium salts of tri-t-butylborohydride, tri-sec-amylborohydride, and tri-isopropylborohydride with lithium tri-sec-butylborohydride being the specific agent of choice. These nucleophilic reagents reduce 4-estren-3-ones with simple efficiency and with a high degree of stereoselectivity.

The trialkylborohydride reducing agents of this invention are prepared by means of an exchange reaction in which a highly hindered trialkylborane is added to a solution of lithium or potassium trimethoxyaluminohydride. The lithium trimethoxyaluminohydride reagent is prepared by the addition of 3 moles of methanol to 1 mole of lithium aluminum hydride in an appropriate solvent, as for example, tetrahydrofuran or ether, cf., Brown and Deck, J. Amer. Chem. Soc. 87, 5620 (1965). The corresponding potassium trimethoxyaluminohydride reagent is prepared by the substitution of potassium aluminum hydride for the lithium aluminum hydride.

The preparation of the lithium trialkylborohydride reagent can be illustrated by the following reaction scheme wherein R' represents a highly hindered alkyl radical:

At ambient temperatures the reaction is essentially complete within 15 minutes; lower temperatures require longer reaction times. Manipulations are performed under an inert gas such as nitrogen or argon. Alternatively, the preferred reagent can be prepared by the reaction of t-butyl lithium with tri-sec-butylborane in an appropriate solvent, as for example, ether, tetrahydrofuran, pentane, hexane, heptane or mixtures thereof.

Once the reagent has been prepared, the temperature of the reaction mixture is adjusted and the estr-4-en-3-one is added, generally in solution. The reaction temperature can vary from −78° C. to 25° C. with the reduction period ranging anywhere from 10 minutes to 8 hours. Preferably, the reduction is initially conducted at −78° C. for a period of 2 hours and then permitted to warm to 0° C., where it is maintained for another 2-hour period. After the reduction is complete, the steroidal borane intermediate which forms is hydrolyzed to the corresponding 3α-alcohol using either an acid or an alkaline hydrolysis. Preferably an alkaline hydrolysis is employed, and even more preferably, the hydrolysis is conducted via the dropwise addition of a solution of sodium hydroxide. An oxidizing agent such as hydrogen peroxide is generally added in order to oxidize the remaining tri-organoborane and to facilitate the separation and removal of the reaction product.

Reduction of 17β-hydroxy-7α-methylestr-4-en-3-one in accordance with this procedure results in the formation of both the 3α,17β-diol and the 3β,17β-diol. Separation of these isomers is achieved by fractional crystallization in ether, the 3α-hydroxy isomer initially crystallizing from solution, whereas the 3α-hydroxy isomer remains in the filtrate. Chromatographic purification of the filtrate using a silica gel column results in the isolation and preparation of appreciable quantities of essentially pure 7α-methylestr-4-ene-3α,17β-diol, as specifically illustrated in Example 5, as compared to the trace quantities which may be present in the reaction mixtures of the prior art.

The term essentially pure as used herein refers to the 3α-hydroxy isomers which are substantially free of their corresponding 3β-hydroxy isomers. More particularly the term essentially pure is used to indicate the fact that the 3α-hydroxy isomers are free of any physiologically significant effects which may be attributable to the corresponding 3β-hydroxy isomers.

Specifically, when referring to the compound 7α-methylestr-4-ene-3α,17β-diol the term essentially pure refers to a material which is at least ten times more active as an antifertility agent in the pregnant hamster test than the prior art 7α-methylestr-4-ene-3β,17β-diol when tested on a weight for weight basis. In addition to the enhanced antifertility activity, essentially pure 7α-methylestr-4-ene-3α,17β-diol has been found to have significantly less associated biological endocrine activity as compared to the corresponding 7α-methylestr-4-ene-3β,17β-diol. Thus a comparison of these two isomers at their respective effective antifertility dosage, indicates the 3β-hydroxy isomer to be 10 times more potent in its anabolic and androgenic side effects and 33 times more potent in its estrogenic side effects than the corresponding 3α-hydroxy isomers. The separation of endocrine and antifertility activities is a highly desirable goal in the search for new antifertility agents. Prolonged usage of androgenic steroids in women results in hirsutism and voice deepening, whereas the estrogenic nature of endocrinologically active steroids plays an adverse role in certain thrombotic disorders, such as thrombophlebitis and pulmonary embolism.

The 7α-methylestr-4-ene-3α,17β-diol when crystallized from an ether solution results in the formation of finely-divided, white crystalline platelets. A comparison of the essentially pure 3α-hydroxy and 3β-hydroxy isomers, crystallized from ether solutions, shows the 3α-hydroxy isomers to melt at a temperature of 171°–6° C., whereas the 3β-hydroxy isomers melts at a temperature of 99°–101° C. Further, a comparison of the nuclear magnetic resonance spectra of these two isomers in completely deuterated dimethylsulfoxide shows a broad doublet at 5.38 δ for the 4-vinyl hydrogen in the 3α-hydroxy isomer, whereas the 3β-isomer shows a broad singlet at 5.24 δ for the 4-vinyl-hydrogen.

Both of the alcohol functions of the 3α,17β-positions can be esterified or etherified using standard chemical procedures. If a free 17β-hydroxy group is present in the starting material, this will also be co-esterified or etherified along with the 3α-hydroxy group to yield the corresponding 3α,17β-diesters or diethers. The 17β-monoesters and monoethers are prepared by initially derivatizing the 17β-position and subsequently reducing the 3-one. The 3α-monoesters and monoethers are prepared by first protecting the 17β- position, reducing the 3-one and derivatizing the resulting 3α-hydroxyl group, and subsequently removing the protecting group from the 17β-position. Varying the mixture of the 17β-substitution prior to reduction and the 3α-substitution subsequent to reduction, results in the formation of mixed esters, ethers and/or ester-ether combinations.

The esters of the present invention are obtained by reacting the hydroxy-steroid with acid anhydrides and acid halides in the presence of a tertiary organic base such as pyridine or triethylamine. In order to prepare the tetrahydropryanyl ethers, dihydropyran is employed in the presence of an acid catalyst such as p-toluenesulfonate.

The 1alkoxycycloalkoxy derivatives of the present invention are prepared by reacting the corresponding steroidal alcohols with a lower alkyl ketal of a cycloalkanone or the lower alkylenolether of a cycloalkanone or a mixture of both in the presence of an acid catalyst such as pyridine p-toluene sulfonate in a suitable solvent such as dioxane, t-butanol or methylene chloride. Temperatures employed may vary from about 0° C. to 70° C. with the lower temperatures being preferred to carry out the reaction. Suitable cycloalkyl derivatives include, for example, cyclopentanone, diethylketal and 1-methoxy-1-cyclohexene. The 1-cycloalkenylethers are prepared directly following essentially the same procedure but substituting higher boiling reaction solvents in order to obtain reaction temperatures above 70° C. Such solvents include benzene and dimethylformamide. Alternatively, the 1-cycloalkenylethers are prepared by a pyrolysis reaction of the isolated 1alkoxycycloalkoxy steroid in a solvent such as toluene, benzene or dimethylformamide. Using conventional techniques the hydroxyl group can be silylated by reacting the steroid with silylating agents such as trialkylchlorosilane, N-trialkylsilylacetamide in the presence of an amine base such as triethylamine or pyridine.

The highly hindered lithium tri-sec-alkylborohydrides do not reduce an esterified or etherified 17β-hydroxyl group to the corresponding alcohol. As long as the reaction conditions and the subsequent isolation procedure remain basic, the 17β-ethers remain stable and are retained. The ester groups at the 17β-position may be hydrolyzed or retained during the hydrolysis and oxidation workup of the reduction mixture, depending upon the temperature conditions. Temperatures below 25° C. during the hydrolysis generally favor retention of the ester group, whereas temperatures above 25° C. can result in ester hydrolysis. Thus, by various esterification and etherification techniques, it is possible to prepare compounds in which the ester or ether derivatives can vary at the 3α- and/or 17β-positions.

The starting materials utilized in the present invention are the compound 17β-hydroxy-7α-methylestr-4-en-3-one and its 17β-derivatives. These compounds are available by the reaction of dimethylcopper lithium with estr-4,6-dien-3-one in an inert solvent, e.g., ether, tetrahydrofuran, hexane or mixtures thereof, at temperatures which range from −78° C. to 25° C. The enolate which initially forms can be quenched with a strong acid such as dilute hydrochloric acid to form the 7α-methyl-4-estren-3-one directly. Alternatively, the enolate can be quenched with a weak protonating agent, as for example, ammonium chloride, to form the 7α-methyl-5-estren-3-one, which can then be isomerized to the 4-ene using either acid or base.

Applicants have discovered that the compounds of the present invention, in particular the compound 7α-methylestr-4-ene-3α,17β-diol, possess marked antiprogestational properties which make them useful as antifertility agents. In women, the typical menstrual cycle is 28 days with the onset of menstruation counted as day 1. By day 12 of the cycle a mature Graafian follicle is ready to rupture and release an ovum. In addition to ovum formation, the follicle also produces estrogen which stimulates the conversion of the uterine endometrium into its proliferative phase. On day 14, the ovum is released and the follicle is converted into the corpus luteum which in addition to estrogen now produces progesterone. These two hormones stimulate the endometrial growth of the uterine lining converting it by day 19 from its proliferative phase into its secretory stage. The ovum is released into the Fallopian tube and is fertilized shortly thereafter. On about day 18½ the fertilized ovum enters the uterus, undergoes a period of uterine migration and by day 21½ to day 24½ the ovum or blastocyst nidates within the uterine lining and begins to implant. This implantation process is completed with the establishment of the fetal-placental circulation occurring at about day 35. Thus, in order for successful implantation to occur, a proper estrogen-progesterone balance is required during the critical period of uterine migration and blastocyst nidation. Subsequent to implantation, rapid placental development occurs and by day 70 to day 75 the placenta now produces all of the progesterone required for the maintenance of pregnancy. Thus, any interference with the normal progesterone requirements of a fertile female during this critical period following fertilization at about day 14 to about day 70 at which there is a decline in ovarian dependence for progesterone, insures the absence of a viable implanted ovum. By insuring the absence of an implanted ovum, estrus in fertile female mammals, or menstrual cyclicity in fertile female primates, including monkeys, baboons and humans, is established.

The antiprogestational effect of these compounds is best demonstrated by observing the decidual cell reaction of a traumatized uterine horn of an immature female rat receiving progesterone. Traumatization of the uterine horn simulates a pseudo-implantation. An increase in tissue weight of the traumatized horn in comparison to the untraumatized contralateral control uterine horn, measures progesterone stimulated growth. Conversely, a reduction of this progesterone-primed decidual response is an in vivo biological measure of the antiprogestational activity of these compounds.

The effect of these compounds upon nidation and implantation is demonstrated by their administration to pregnant hamsters at a point immediately prior and subsequent to nidation and observing their prepartum effects. Mated female hamsters, considered to be pregnant by the presence of sperm in a post-estrus vaginal lavage, are treated subcutaneously with the test compound during days 3–8 of pregnancy. This period of gestation in the hamster relates in the human from a point just prior to implantation of a fertilized ovum to a point after which implantation has occurred and placental circulation is now complete. Treated animals are sacrificed one day prior to parturition and the total number of live feti is compared to those in a control group of mated fertile female hamsters.

The term fertile female mammal as used herein refers to any female mammal that can reproduce and that requires progesterone for reproduction and gestation. Illustrative of such species are mice, rats, guinea pigs, rabbits, ferrets, dogs, cats, cows, horses and primates, including monkeys, baboons and humans.

The 7α-methylestr-4-ene-3α,17β-diols of the present invention are variously administered in order to achieve their antiprogestational effect. In women, they can be administered in small daily doses, i.e., a "mini-pill" type of regimen, without inhibiting or interfering with normal ovulation. When administered in this fashion, the maturation of the uterine lining is forced out of phase with the ovulation process, thereby preventing nidation or implantation of the fertilized egg. Alternatively, the 7α-methylestr-4-ene-3α,17β-diols can be administered in one or more weekly or monthly doses and most effectively during the period of from about day 14 to about day 70 from menses.

The contranidative effect of these compounds can be utilized to insure the failure of a fertilized ovum to implant in any fertile female mammal as previously defined. Thus, the present invention is useful for controlling fertility in such commercially valuable species as dogs, cats, cows and horses. Generally, the compounds are administered for a period of time not exceeding 50% of the gestation period for the particular species, and preferably these compounds are administered during the first quarter of their gestation period.

The particular dosage of the active ingredient depends upon such factors as the route of administration, age, weight of the mammal being treated and the frequency of dosing. Dosage units for treatment in humans using a "mini-pill" type of regimen contain from 0.1 mg to 1.0 mg, depending upon the particular steroid employed. Preferably a dosage unit of from 0.1 mg to 0.5 mg, and even more particularly a dosage unit from 0.1 mg to 0.25 mg. is employed. A weekly or monthly dosage unit of the therapeutic steroid contains from about 0.1 mg to about 3.0 g of the active ingredient per administration with doses repeated as necessary. In the case of a subcutaneous depot preparation or a medicated intrauterine device, amounts up to 3.0 g of the active ingredient can be administered once or twice a year.

The compounds of the present invention are administered in various dosage unit forms such as tablets, capsules, powders, granules, oral solutions or suspensions, sterile solutions or suspensions for parenteral use, sublingual and intrabuccal preparations, intravaginal and rectal suppositories, vaginal or intrauterine devices impregnated with the active ingredient, subcutaneous and intramuscular implants and depot preparations. The following specific examples further illustrate the invention.

EXAMPLE 1

3,17β-Diacetoxyestr-3,5-diene

The compound 19-nortestosterone, 400 g, is refluxed under nitrogen in a mixture of 1500 ml of acetic anhydride and 1500 ml of acetyl chloride for a period of 3 hours. The volatile solvents are distilled at atmospheric pressure and the final traces of solvent removed under reduced pressure. The solid residue which remains is triturated with ice water, filtered, washed with cold aqueous sodium bicarbonate solution, rinsed with water and dried. Two recrystallizations of this residue from acetone yield 370 g of 3,17β-diacetoxyestr-3,5-diene which melts at 165°–71° C.

EXAMPLE 2

17β-Hydroxyestra-4,6-dien-3-one acetate

The compound 3,17β-diacetoxyestr-3,5-diene, 60.0 g (0.158 mole) prepared as in Example 1, is placed in an acetone buffered solution containing 3,180 ml of acetone, 816 ml of water, 81.6 ml of acetic acid, 18 ml of pyridine, and 81.6 g of sodium acetate. The solution is cooled to 0°–5° C. using a salt-methanol-ice bath and 32.1 g (0.18 mole) of N-bromosuccinimide is added at one time. The reaction mixture is totally shielded from light and stirring continued for a period of 3 hours at 0°–5° C. The solution is poured onto 12 liters of cold brine and the product extracted with 1 liter of ether. The ether extract is washed with water, dried over anhydrous magnesium sulfate and concentrated under vacuum at temperatures below 20° C. The amber oil residue is dissolved in 75 ml of dimethylformamide and rapidly added to a vigorously refluxing suspension of 750 ml of dimethylformamide, 60 g of lithium bromide and 60 g of lithium carbonate under nitrogen. Residual ether is permitted to evaporate and the reaction mixture is refluxed for a period of one hour. On cooling, the suspension is filtered and the filtrate is poured into an ice-water mixture. The product is extracted into ether and the combined ether extracts are washed with water, 2 liters of a 5% sodium hydroxide solution and washed again with water. The solution is dried over anhydrous magnesium sulfate and concentrated under vacuum to yield a yellow solid which is layered with hexane and filtered to yield 34.6 g of the desired 17β-hydroxy-estra-4,6-dien-3-one acetate.

EXAMPLE 3

17β-Hydroxy-7α-methylestr-4-en-3-one acetate

A solution of lithium dimethylcopper is prepared under nitrogen by the addition of 1 mole of 1.6 M ethereal methyllithium to a slurry of 99 g (0.52 mole) of cuprous iodide contained in 1000 ml of anhydrous ether at 0° C. The solution is stirred at this temperature for 5 minutes and a solution of 35 g (0.11 mole) of 17β-hydroxyestra-4,6-dien-3-one acetate, prepared as in Example 2, contained in 300 ml of anhydrous tetrahydrofuran is added over a 10 minute period. The reaction mixture is stirred for an additional 15 minutes at 0° C. and poured into a saturated aqueous ammonium chloride solution. Benzene is added and the resulting mixture is rapidly filtered through diatomaceous earth. The organic layer is washed with a saturated aqueous ammonium chloride solution, with water, dried over anhydrous magnesium sulfate and evaporated to dryness. The crude product is layered with hexane and cooled overnight to yield 25 g of 17β-hydroxy-7α-methyl-estr-5-en-3-one acetate.

A 7 g portion of this material is dissolved in 170 ml of methanol to which 7 ml of water and 10 ml of concentrated hydrochloric acid have been added. The solution is stirred for a period of 2 hours and poured onto a mixture of ice-water. The ether extract is washed with water, dried over magnesium sulfate and evaporated to dryness. Recrystallization of the residue from acetone-hexane yields the desired 17β-hydroxy-7α-methylestr-4-en-3-one acetate, which melts at 108°–110° C.

EXAMPLE 4

17β-Hydroxy-7α-methylestr-4-en-3-one

The compound 17β-hydroxy-7α-methylestr-4-en-3-one acetate, prepared in accordance with the preceding Example, is dissolved in 400 ml of methanol containing 9.5 g of sodium methoxide. The yellow solution is stirred for 2 hours at room temperature under nitrogen and poured onto an ice-water mixture. The solid which forms is filtered and recrystallized from an acetone-hexane mixture to yield 11.3 g (two crops) of 17β-hydroxy-7α-methylestr-4-en-3-one having a melting point of 144°–6° C.

EXAMPLE 5

7α-Methylestr-4-ene-3α,17β-diol

To 60 ml of a 1 molar solution of lithium aluminum hydride in tetrahydrofuran, cooled in an ice bath, is added 7.88 ml (0.18 mole) of methanol. The solution is stirred for 30 minutes following which 15 ml (0.06 mole) of tri-sec-butylborane is added with additional stirring continued for 30 minutes at 0° C. The reducing agent prepared in this manner is cooled in a dry ice-acetone bath to about −78° C. and 5.75 g (0.02 mole) of 17β-hydroxy-7α-methylestr-4-en-3-one in 150 ml of tetrahydrofuran is slowly added. The reaction mixture is stirred for a period of two hours at this temperature, warmed to 0° C. and stirring continued for an additional two hours. The reaction mixture is decomposed by the addition of 30 ml of 3N sodium hydroxide followed by 30 ml of a 30% hydrogen peroxide solution. Solid potassium carbonate is added and the tetrahydrofuran decanted. The solid residue is washed with 2 additional 150 ml portions of tetrahydrofuran. The combined tetrahydrofuran solutions are dried over anhydrous sodium sulfate, filtered and the solvent removed. The residue is taken up in a large volume of ether, filtered, concentrated and cooled. The 7α-methylestr-4-ene-3β,17β-diol which separates on cooling is recrystallized twice from ether to yield 3.5 g of a white, crystalline material which melts at 96°–102° C.

The mother liquors from the above crystallizations are combined and evaporated to dryness. The residue is dissolved in methylene dichloride and chromatographed on a silica gel column (60-200 mesh) which removes small amounts of the remaining 3β-hydroxy isomer. The desired 7α-methylestr-4-ene-3α,17β-diol is eluted with ether, and the eluate recrystallized twice from ether to yield 1.3 g of finely divided, white, crystalline platelets melting at 171°–6° C.

Following essentially the same procedure by substituting the compounds 17β-hydroxy-7α-methylestr-4-en-3-one acetate, 7α-methyl-17β-trimethylsiloxy-estr-4-en-3-one and 17β-(1'-methoxycyclohexyloxy)-7α-methylestr-4-en-3-one for the 17β-hydroxy-7α-methylestr-4-en-3-one above, results in the formation of 7α-methylestr-4-ene-3α,17β-diol 17-acetate, 7α-methyl-17β-trimethylsiloxy-estr-4-en-3α-ol and 17β-(1'-methoxycyclohexyloxy)-7α-methylestr-4-en-3α-ol, respectively.

EXAMPLE 6

7α-Methyl-17β(2'-tetrahydropyranyloxy)-estr-4-en-3α-ol

Phosphorous oxychloride is added to a solution of 17β-hydroxy-7α-methylestr-4en-3-one in 2,3-dihydropyran. After standing at room temperature for a period of 72 hours, the solution is diluted with ether, washed with aqueous sodium carbonate followed by a water wash, dried over sodium sulfate and evaporated to dryness under vacuum. The residue which contains 7α-methyl-17β-(2'-tetrahydropyranyloxy)estr-4-en-3-one is dissolved in tetrahydrofuran and reduced with lithium tri-sec-butylborohydride following essentially the same procedure as in Example 1. The residue is taken up in a large volume of ether and fractionally crystallized to remove the 3β-hydroxy isomer. The mother liquors are concentrated to dryness. The residue is dissolved in a minimum amount of methylene dichloride, placed on a silica gel column and eluted with ether. The eluate is evaporated to dryness and the residue crystallized from ether to yield 7α-methyl-17β(2'-tetrahydropyranyloxy)estr-4-en-3α-ol.

EXAMPLE 7

7α-Methylestr-4-ene-3α,17β-diol diacetate

The compound 7α-methylestr-4-ene-3α,17β-diol, prepared as in Example 5, is dissolved in acetic anhydride and pyridine. After 18 hours standing at room temperature, the reaction mixture is poured into water. The solid is filtered and crystallized from acetone to yield 7α-methylestr-4-ene-3α,17β-diol diacetate.

EXAMPLE 8

7α-Methyl-3α-(1'-methoxycyclohexyloxy)estr-4-en-17β-ol acetate

The compound 7α-methylestr-4-en-3α,17β-diol 17-acetate is dissolved in anhydrous dioxane and treated with pyridine, p-toluenesulfonate and cyclohexanone methyl enolether. Stirring is continued for a period of 3 hours. The solvent is removed in vacuo and the residue is crystallized from pentane resulting in the formation of the desired 7α-methyl-3α-(1'-methoxycyclohexyloxy)estr-4-en-17β-ol acetate.

EXAMPLE 9

Antiprogestational Activity

Groups of ten immature female rats are treated over a nine day period at age 28–36 days. One group of ten animals receives a daily dosage of 40 mg/kg of progesterone. A second group of ten animals receives 40 mg/kg of progesterone and in addition concurrently receives 1 mg/kg of the test compound, 7α-methylestr-4-ene-3α,17β-diol. A third group of ten animals serves as the vehicle control group. At day 32 of treatment the right uterine horn of all animals is traumatized with a burred needle to simulate pseudo-implantation. The animals are sacrificed at day 37 of age and the uterine horns, both the untraumatized control uterine horn and the traumatized horn are separately weighed. The mean uterine horn weight increase of the traumatized horn over the untraumatized horn in animals receiving the drug plus progesterone was 26% of the corresponding progesterone treated control group, indicating that 7α-methylestr-4-ene-3α,17β-diol possesses marked antiprogestational properties.

EXAMPLE 10

Antifertility Activity

Commercially available female hamsters are mated and made pregnant by cohabitating with males overnight. Vaginal smears are taken on the following morning to see if they are sperm positive. A positive smear indicates day 1 of pregnancy. Test animals are placed in groups of eight with two to three animals per cage under conditions which enable a control of temperature, humidity, air flow, feed and water. The test group of animals are treated on days 3,4,5,6,7 and 8 of pregnancy with the test compound by subcutaneous administration. This period of treatment in the hamster roughly corresponds in the fertile human female from a point prior to implantation to a point subsequent to the ovarian-placental shift, i.e., the point at which placental circulation is complete. Treatment and vehicle only control groups are sacrificed on day 15 of pregnancy. At necropsy each animal is classified as pregnant with live feti, as not pregnant with resorbed uterine implantation sites, or as not pregnant with no evidence of conception having taken place. The antifertility activity is indicated by a decrease in the total number of live feti in the treatment group as compared to those in the vehicle control group.

Using this test system the compound 7α-methylestr-4-ene-3α,17β-diol when administered subcutaneously at a dosage level of 1.0 mg/kg during the period of days 3 through 8 of pregnancy, exhibits a high antifertility activity with no live feti present at day 15, one day prior to parturition. In contrast thereto, when the compound 7α-methylestr-4-ene-3β,17β-diol is administered under identical conditions of treatment and dosage, 29 live feti are obtained at day 15. Following the same procedure but increasing the dosage level of 10.0 mg/kg the 3β-hydroxy isomer resulted in no live feti at day 15. Thus, in this test system, 7α-methylestr-4-ene-3α,17β-diol demonstrates a ten-fold increase in its antifertility effects as compared to the corresponding 7α-methylestr-4-ene-3β,17β-diol isomer.

We claim:

1. A method of controlling fertility in fertile female mammals which comprises the administration to said mammals of a therapeutically effective amount of an essentially pure 7α-methylestr-4-ene-3α,17β-diol having the formula:

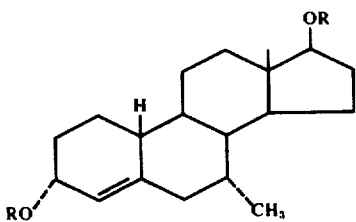

where in each R is selected from the group consisting of hydrogen, acyl having from 1 to 12 carbon atoms, 1-cycloalkenyl having from 5 to 8 carbon atoms, 1-methoxycycloalkyl and 1-ethoxycycloalkyl in which the cycloalkyl group has from 5 to 8 carbon atoms, 2-tetrahydropyranyl, and trialkylsilyl in which the alkyl group contains from 1 to 4 carbon atoms.

2. A method of claim 1 in which the compound is administered in a total daily dosage of from 0.1 mg to 3.0 g.

3. A method of claim 1 in which the fertile female is a human female and the compound is 7α-methylestr-4-ene-3α,17β-diol.

4. A method for insuring the absence of implantation of an ovum in fertile female mammals which comprises administering to such mammals a therapeutically effective amount of the compound of claim 1 for a period not exceeding the first half of said mammal's gestation period.

* * * * *

UNITED STATES PATENT AND TRADEMARK OFFICE
CERTIFICATE OF CORRECTION

PATENT NO. : 4,000,273
DATED : December 28, 1976
INVENTOR(S) : Joyce F. Grunwell and Harvey D. Benson It is certified that error appears in the above-identified patent and that said Letters Patent are hereby corrected as shown below:

Column 4, line 24, "3α-isomer" should read "3β-isomer".

Column 5, line 46, "3α-hydroxy" should read "3β-hydroxy".

Signed and Sealed this twelfth Day of July 1977

[SEAL]

Attest:

RUTH C. MASON
*Attesting Officer*

C. MARSHALL DANN
*Commissioner of Patents and Trademarks*